(12) United States Patent
Jung et al.

(10) Patent No.: US 11,978,975 B2
(45) Date of Patent: May 7, 2024

(54) SPRING CONTACT RING

(71) Applicant: Heraeus Deutschland GmbH & Co. KG, Hanau (DE)

(72) Inventors: Markus Jung, Hanau (DE); Josef Roth, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 63 days.

(21) Appl. No.: 17/649,991

(22) Filed: Feb. 4, 2022

(65) Prior Publication Data
US 2022/0255254 A1    Aug. 11, 2022

(30) Foreign Application Priority Data
Feb. 8, 2021    (DE) .......................... 102021102864.7

(51) Int. Cl.
*H01R 13/11*   (2006.01)
*A61N 1/375*   (2006.01)
*H01R 13/03*   (2006.01)

(52) U.S. Cl.
CPC .......... *H01R 13/111* (2013.01); *A61N 1/3752* (2013.01); *H01R 13/03* (2013.01); *H01R 2201/12* (2013.01)

(58) Field of Classification Search
CPC .... A61N 1/3752; H01R 13/03; H01R 13/111; H01R 2201/13
USPC ................................................ 439/843, 842
See application file for complete search history.

(56) References Cited

U.S. PATENT DOCUMENTS

| 3,858,962 A | * | 1/1975 | Bonhomme | H01R 13/17 |
| | | | | 439/843 |
| 4,714,441 A | * | 12/1987 | Corman | H01R 13/187 |
| | | | | 439/842 |
| 4,753,616 A | * | 6/1988 | Molitor | H01R 13/17 |
| | | | | 439/825 |
| 5,203,813 A | * | 4/1993 | Fitzsimmons | H01R 43/16 |
| | | | | 439/843 |
| 5,261,840 A | * | 11/1993 | Benz | H01R 4/4881 |
| | | | | 439/843 |
| 5,730,628 A | * | 3/1998 | Hawkins | A61N 1/3752 |
| | | | | 439/843 |

(Continued)

FOREIGN PATENT DOCUMENTS

| CN | 110732083 A | | 1/2020 |
| DE | 102019112226 B3 | * | 10/2020 |

(Continued)

*Primary Examiner* — Marcus E Harcum
(74) *Attorney, Agent, or Firm* — Dicke, Billig & Czaja, PLLC

(57) ABSTRACT

The present invention relates to a monolithic spring contact ring, preferably for use in a medical electrode, comprising an outer ring and a plurality of elastically deformable belt-shaped spring elements, each comprising two curved connectors which form a continuously running, gap-free connection between the outer ring and the respective spring element, wherein the spring elements each extend continuously from the first connector to the second connector via a first bend, a central part of the spring element and a second bend, wherein the middle part comprises a front side which points in the direction of the central axis of the outer ring.

15 Claims, 3 Drawing Sheets

(56) References Cited

U.S. PATENT DOCUMENTS

| | | | | |
|---|---|---|---|---|
| 5,735,716 | A * | 4/1998 | Bilezikjian | H01R 13/187 439/843 |
| 6,102,746 | A * | 8/2000 | Nania | H01R 24/40 439/675 |
| 6,540,568 | B2 * | 4/2003 | Miyazaki | H01R 13/6583 439/852 |
| 6,547,607 | B2 * | 4/2003 | Moll | H01R 13/187 439/843 |
| 7,074,096 | B2 * | 7/2006 | Copper | H01R 43/16 439/841 |
| 7,587,244 | B2 * | 9/2009 | Olbertz | A61N 1/3752 607/37 |
| 7,803,021 | B1 * | 9/2010 | Brase | H01R 24/58 439/668 |
| 8,057,269 | B2 * | 11/2011 | Ledermann | H01R 13/187 439/843 |
| 8,062,063 | B2 * | 11/2011 | Malloy | H01R 13/187 439/578 |
| 8,078,280 | B2 * | 12/2011 | Sage | H01R 13/18 439/843 |
| 8,428,724 | B2 * | 4/2013 | Sage | A61N 1/3605 607/37 |
| 8,579,666 | B2 * | 11/2013 | Lampert | H01R 13/187 439/843 |
| 8,678,843 | B2 * | 3/2014 | Jullien | H01R 24/58 439/283 |
| 8,731,670 | B2 * | 5/2014 | Osypka | A61N 1/3752 607/37 |
| 8,731,671 | B2 * | 5/2014 | Rodby | H01R 13/187 607/36 |
| 9,095,728 | B2 * | 8/2015 | Janzig | H01R 43/16 |
| 9,278,224 | B1 * | 3/2016 | Vadlamudi | H01R 13/187 |
| 10,050,358 | B2 * | 8/2018 | Müller | H01R 13/111 |
| 10,933,233 | B2 | 3/2021 | Leitold et al. | |
| 11,462,848 | B2 * | 10/2022 | Listing | H01R 13/187 |
| 2003/0176115 | A1 * | 9/2003 | Suess | H01R 13/187 439/843 |
| 2005/0033138 | A1 | 2/2005 | Ries et al. | |
| 2007/0066152 | A1 * | 3/2007 | Mohs | H01R 13/187 439/843 |
| 2008/0246231 | A1 * | 10/2008 | Sjostedt | A61N 1/0551 29/428 |
| 2008/0255631 | A1 * | 10/2008 | Sjostedt | A61N 1/3752 607/37 |
| 2009/0036003 | A1 * | 2/2009 | Morana | H01R 13/187 439/843 |
| 2009/0061700 | A1 * | 3/2009 | Coe | H01R 13/187 439/843 |
| 2010/0191299 | A1 * | 7/2010 | Ayzenberg | H01R 13/187 439/682 |
| 2011/0022102 | A1 | 1/2011 | Rey et al. | |
| 2011/0264162 | A1 * | 10/2011 | Osypka | A61N 1/3752 439/668 |
| 2011/0270330 | A1 | 11/2011 | Janzig et al. | |
| 2011/0270363 | A1 * | 11/2011 | Schramm | A61N 1/3752 29/858 |
| 2012/0129409 | A1 * | 5/2012 | Drew | A61N 1/3752 219/121.64 |
| 2013/0110204 | A1 * | 5/2013 | Lim | A61N 1/3752 607/72 |
| 2014/0148885 | A1 | 5/2014 | DeRohan et al. | |
| 2014/0237806 | A1 | 8/2014 | Smith et al. | |
| 2015/0375002 | A1 | 12/2015 | Janzig et al. | |
| 2017/0151439 | A1 | 6/2017 | Malinowski | |
| 2018/0028820 | A1 * | 2/2018 | Nageri | A61N 1/37235 |
| 2019/0103696 | A1 | 4/2019 | Conger | |
| 2019/0288433 | A1 * | 9/2019 | Wang | H01R 13/2478 |
| 2020/0155827 | A1 | 5/2020 | Li et al. | |
| 2020/0330772 | A1 * | 10/2020 | Hartmann-Bax | A61N 1/3752 |
| 2020/0350720 | A1 * | 11/2020 | Carter | H01R 13/17 |

FOREIGN PATENT DOCUMENTS

| | | |
|---|---|---|
| EP | 2614856 A1 | 7/2013 |
| EP | 3530314 | 8/2019 |
| WO | 2012027125 A1 | 3/2012 |
| WO | 2013070875 A1 | 5/2013 |
| WO | 2015134859 A1 | 9/2015 |
| WO | 2018022455 A1 | 2/2018 |
| WO | 2019217415 A1 | 11/2019 |

* cited by examiner

SPRING CONTACT RING

CROSS-REFERENCE TO RELATED APPLICATIONS

This application claims priority pursuant to 35 U.S.C. 119(a) to German Patent Application No. 102021102864.7, filed Feb. 8, 2021, which application is incorporated herein by reference in its entirety.

FIELD OF THE INVENTION

The invention relates to a spring contact ring, which can be used in particular in the field of medical technology, for example in pulse generators which are used in connection with active implantable medical devices.

TECHNICAL BACKGROUND

Spring contact elements serve to connect two different electrical components. In the field of medical technology, special demands are made on the reliability of these components. For example, such a contact element should ensure a stable electrical connection even after the contact pin has been inserted and removed multiple times. An exemplary spring contact element for use in the field of medical technology is disclosed in EP2614856A1. Contact elements used in the prior art usually consist of several components and are therefore more susceptible to errors due to their design. In addition, they are often complicated to manufacture.

PREFERRED EMBODIMENTS

The object of the present invention is to solve one or more of the problems mentioned above and further problems of the prior art. For example, the invention enables a simple and cost-effective manufacture of highly reliable spring contact rings.

These objects are achieved by the methods and devices described herein, particularly those described in the claims.

Preferred embodiments of the invention are described below.

Monolithic spring contact ring, preferably for use in a medical electrode, comprising an outer ring and a plurality of elastically deformable belt-shaped spring elements, each comprising two curved connectors, which form a continuously running, gap-free connection between the outer ring and the respective spring element, wherein the spring elements each extend continuously from the first connector to the second connector via a first bend, a central part of the spring element and a second bend, wherein the central part comprises a front side pointing in the direction of the central axis of the outer ring.

Spring contact ring according to Embodiment 1, wherein the central part is delimited and defined by the first bend and the second bend.

Spring contact ring according to either of the preceding embodiments, wherein the central part has a shape which is at a uniform distance from the central axis of the outer ring.

Spring contact ring according to any one of the preceding embodiments, wherein the front side has a surface parallel to the outside of the outer ring or is conical or undulating.

Spring contact ring according to any one of the preceding embodiments, wherein the spring elements are arranged and configured such that essentially only radial deformation forces act on the spring elements when a cylindrical contact pin is inserted into the spring contact ring.

Spring contact ring according to any one of the preceding embodiments, wherein the spring elements are arranged and configured such that the spring constant of the spring elements is significantly determined by the degree of curvature of the two connectors and/or of the two bends.

Spring contact ring according to any one of the preceding embodiments, wherein the spring elements are arranged and configured such that the spring constant of the spring elements is largely determined by their wall thickness.

Spring contact ring according to any one of the preceding embodiments, wherein the front side comprises a thread.

Spring contact ring according to any one of the preceding embodiments, wherein the front side comprises a section with increased wall thickness.

Spring contact ring according to any one of the preceding embodiments, wherein the outer ring comprises Pt or a Pt alloy, preferably PtIr.

Spring contact ring according to any one of the preceding embodiments, wherein the spring elements comprise MP35N.

Spring contact ring according to any one of the preceding embodiments, which comprises exactly 2, 3, or 4 similar spring elements.

Spring contact ring according to any one of the preceding embodiments, which comprises no other spring element than the said spring elements.

Spring contact ring according to any one of the preceding embodiments, wherein the bends have an increasing or decreasing wall thickness in the direction of the outer ring.

Medical pulse generator or detector, comprising a spring contact ring according to any one of the preceding embodiments.

BRIEF DESCRIPTION OF THE DRAWINGS

Further features, advantages and possible applications of the present invention follow from the following description of the exemplary embodiments and the figures. All features described and/or illustrated form the subject-matter of the invention per se and in any combination, also independently of their composition in the individual claims or their back-references. In the figures, like reference numerals designate like or similar objects.

DETAILED DESCRIPTION

Figure 1:
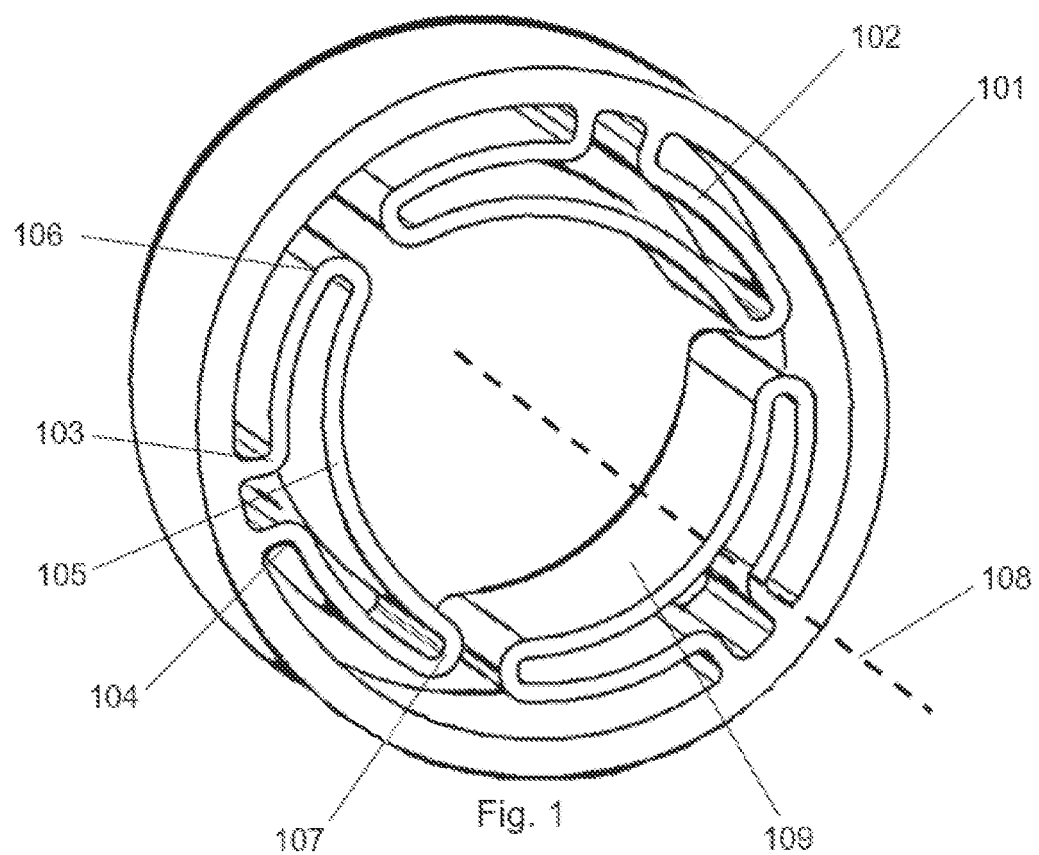
FIG. 1 shows a perspective view of a spring contact ring according to the invention.

In principle, for the embodiments described herein, the elements of which "have" or "comprise" a particular feature (e.g., a material), a further embodiment is always contemplated in which the element in question consists solely of the feature, i.e. comprises no further components. The word "comprise" or "comprising" is used herein synonymously with the word "have" or "having" and does not preclude the presence of further features.

If an element is referred to in the singular in an embodiment, an embodiment is also contemplated in which a plurality of these elements is present. The use of a term for an element in the plural fundamentally also encompasses an embodiment in which only a single corresponding element is contained.

Unless otherwise indicated or clearly precluded from the context, it is possible in principle, and is herewith clearly taken into consideration, that features of different embodiments may also be present in the other embodiments described herein. It is also contemplated in principle that all features that are described herein in conjunction with a method can also be present in and applicable to the products and devices described herein, and vice versa. Only for reasons of succinct presentation are all such contemplated combinations not explicitly listed in all instances. Technical solutions which are known to be equivalent to the features described herein are also intended to be encompassed in principle by the scope of the invention.

In a first aspect, a monolithic spring contact ring is described which is preferably suitable for use in a medical electrode. The spring contact ring comprises an outer ring and a plurality of elastically deformable belt-shaped spring elements. These belt-shaped spring elements each comprise two curved connectors. These connectors form a continuously extending, gap-free connection between the outer ring and the respective spring element. The spring elements each extend continuously from the first connector to the second connector via a first bend, a central part of the spring element, and a second bend. The central part comprises a front side pointing in the direction of the central axis of the outer ring.

The spring contact ring according to the invention is monolithic, i.e., it consists of a single material or a solid material composite which does not have to be assembled individually from several components. The spring elements are belt-shaped, i.e. their cross-section is not circular but rather, for example, D-shaped or approximately rectangular. The spring elements preferably have a flat surface in the direction of the central axis, or a surface with only a slight curvature, for example a curvature that is not substantially greater than the curvature of the outer ring. This results a relatively large contact surface when the spring elements form an electrical connection with an inserted contact pin. The belt-shaped spring elements can thus form a larger-area contact with a contact pin than is the case with spring contacts in the prior art, in which the corresponding spring elements are formed by a wire. The spring elements are elastically deformable, i.e. they can be deformed by insertion of a contact pin, but after the contact pin has been removed from the spring contact ring they are essentially completely restored to their original shape. This is important so that a stable electrical connection is ensured even with frequent use of the spring contact ring, i.e. after the contact pin has been inserted and removed multiple times.

Due to the elastic deformability of the spring elements, the inner diameter of the spring contact defined by the front sides of the central parts of the spring elements will not change, or change only slightly, if a contact pin with a diameter larger than this inner diameter is inserted into the spring element and removed again. For example, the inner diameter of the spring contact will change by less than 5%, preferably less than 4%, 3%, 2% or less than 1% relative to the original inner diameter of the spring contact after a contact pin has been inserted and removed again once.

The spring elements are each connected to the outer ring via two curved connectors. The first connector and the second connector are each arranged directly on the outer ring. The spring elements preferably have a continuous shape, i.e. they do not have an open end. The spring elements comprise a central part, which is delimited by two bends in the spring element. These bends are not identical to the connectors. The spring elements preferably comprise a total of four curved areas, namely two curved connectors and two bends, wherein the latter jointly define the central part of the spring elements. The central part comprises a front side pointing in the direction of the central axis of the outer ring. The front side of the central part is preferably arranged and configured to establish an electrical connection with a contact pin which can be inserted into the spring contact ring.

The first connector and the first bend are preferably curved in opposite directions to one another. The second connector and the second bend are preferably curved in opposite directions to one another. This means that a connector and the respectively adjacent bend together form a shape that in cross-section resembles the letter S or the numeral 2.

The outer diameter of a spring contact ring can be, for example, 0.1 to 10 mm, preferably 0.3 to 3 mm. In relation to the area between the front sides of the spring elements, the inner diameter can be, for example, 0.01 to 9 mm, preferably 0.04 to 4 mm. The length of a spring contact ring along the central axis can be, for example, 0.05 to 20 mm or preferably 0.1 to 10 mm. The wall thickness of the outer ring can be, for example, 0.01 to 3 mm or preferably 0.03 to 1 mm.

In a preferred embodiment, the central part has a shape which is at a uniform distance from the central axis of the outer ring. By this is meant that the front side of the central part of the spring element is everywhere at essentially the same distance from the central axis of the outer ring, ie at practically all surface positions on the front side. In this way, a particularly large contact surface can be provided for the connection to a contact pin.

The front side of the central part of the spring element can be designed such that its shape substantially corresponds to a section of a lateral surface of a cylinder. The front side may, for example, be designed and arranged substantially parallel to the outside of the outer ring, i.e., the side of the outer ring distal with respect to the central axis of the outer ring. In some embodiments, the front side of the central part of the spring element may be conically tapered, i.e. it is arranged, for example, at an angle to the central axis of the outer ring which differs from 0°. In such an embodiment, insertion of a contact pin into the spring contact ring can be facilitated. In some embodiments, the front side of the central part of the spring element has the shape of a surface that is uniformly curved, i.e. similar to the lateral surface of a cylinder. In other embodiments, the front side of the central part of the spring element has an undulating surface. In some embodiments, such an undulating surface can be configured and set up so that when a cylindrical contact pin is inserted, it merges into a shape that is no longer undulating but rather uniformly curved, so that during insertion it adapts to the shape of the contact pin.

The spring elements are preferably arranged and configured so that essentially only radial deformation forces act on the spring elements when a cylindrical contact pin is inserted into the spring contact ring. This can be achieved, for example, by a suitable arrangement of the first bend and the second bend of the spring element.

The first bend and the second bend of a spring element, which connect the spring element to the outer ring, are preferably arranged in the direction of the central axis of the outer ring at the same longitudinal position of the outer ring. The position of the first bend and the second therefore preferably differ essentially only in the radial direction of the outer ring. The first bend and the second bend are preferably arranged at two positions of the outer ring which lie in a common transverse plane with respect to the major axis of the outer ring.

In one embodiment, the spring elements are arranged and configured so that the spring constant of the spring elements is significantly determined by the degree of curvature of the two connectors and/or of the two bends. In one embodiment, the spring constant of a spring element is mainly determined by the degree of curvature of the two connectors of the spring element. This means that other geometric features of the spring element, in particular the curvature of other parts of the spring element, play only a substantially subordinate role in setting the spring force of the spring element. For example, by varying the degree of curvature of the two connectors and/or of the two bends, the spring constant of a spring element can be changed by at least 5% or preferably by at least 10%.

In one embodiment, the spring elements are arranged and configured so that the spring constant of the spring elements is largely determined by their wall thickness. For example, the spring constant of the spring elements can be set by the thickness of the first bend and of the second bend of the spring elements. However, the spring constant can also be influenced by the thickness of the front side. In some embodiments, the front side comprises a section with increased wall thickness for this purpose. This means that the front side has overall different wall thicknesses in different positions, for example a greater wall thickness in the middle of the front side as compared to the edge areas of the front side. For example, by changing the wall thickness of the spring element, the spring constant of a spring element can be changed by at least 5% or preferably by at least 10%.

In some embodiments, the front side of the central part of the spring element may comprise a thread. This makes it possible for a contact pin with a correspondingly matching thread to be screwed into the spring contact ring. Such a thread can be formed by groove-shaped depressions or recesses in the front side of the central part. In one embodiment, these recesses are designed to be continuous, i.e., they interrupt the front side in such a way that the recesses extend in the radial direction over the entire thickness of the front side. In one embodiment, the thread is formed by incisions in the front side of the central part. The fixation of a contact pin can be improved by a thread, and in particular a displacement of the contact pin along the central axis of the spring contact ring can be prevented.

The contact ring according to the invention may comprise, for example, one or more of the metals selected from the list consisting of Pt, Ir, Ta, Pd, Ti, Au, Cu, Ag, Mo, Nb, W, Ni, MP35N, 316L, 301, 304 and spring steel. The spring contact ring can also comprise multilayer material systems made of these metals.

In some embodiments, the outer ring comprises or consists of Pt or a Pt alloy, preferably PtIr. Examples of PtIr include PtIr10 and PtIr20. PtIr10 is an alloy of 88 to 92% platinum and 8 to 12% iridium.

PtIr20 is an alloy of 78 to 82% platinum and 18 to 22% iridium.

In some embodiments, the spring elements may comprise or consist of MP35N. MP35 is a hardenable nickel-cobalt-based alloy. A variant of MP35 is described in industry standard ASTM F562-13. In one embodiment, MP35 is an alloy comprising 33 to 37% Co, 19 to 21% Cr, 9 to 11% Mo, and 33 to 37% Ni.

In one embodiment, the outer ring and the spring elements comprise an identical material. In one embodiment, the outer ring and the spring elements consist of the same material. In one embodiment, the outer ring comprises Pt or a Pt alloy, and the spring elements comprise MP35N. The outer ring and the spring elements may either be formed from the same workpiece or they may be assembled from several components to form a monolithic composite. For example, the outer ring can be welded to the spring elements or by means of diffusion bonding firmly bonded to each other using a drawing process. In any case, the overall structure of the spring contact ring is monolithic, i.e. the outer ring and the spring elements form a bonded composite with one another. Diffusion bonding is generally understood to mean a process in which two bodies of different materials which are otherwise difficult to connect to one another are brought into a stable connection. Here two different materials are brought into contact under suitable temperature and pressure conditions and are kept under these conditions for a certain period of time. Under these temperatures and pressures, which are usually elevated compared to normal conditions, on the connecting surface of the two materials, a mass transfer takes place between the two bodies, which can create a very stable connection between the two bodies.

A spring contact ring according to the invention may comprise a plurality of several similar spring elements, for example exactly 2, 3, or 4 similar spring elements, as described herein.

In some embodiments, the spring contact ring is configured to contact a contact pin via the spring elements described herein. In some embodiments, the spring contact ring does not comprise any spring element other than the spring elements according to the invention described herein. This means that all spring elements contained in the spring contact ring, which are configured to exert a spring force on a contact pin, are spring elements according to the invention, as they are described herein.

In one embodiment, the bends of a spring element have a wall thickness that increases in the direction of the outer ring, i.e., they taper in the direction of the central axis of the outer ring, but are designed to be thicker at the direct transition to the outer ring. In one embodiment, the bends of a spring element have a wall thickness that decreases in the direction of the outer ring, i.e., they taper in the direction of the outer ring, but are designed to be thicker in the direction of the central axis of the spring contact ring.

The spring contact ring is preferably configured to form a total of at least three contact points between the spring elements and an inserted cylindrical contact pin. For this purpose, the spring contact ring can comprise at least three spring elements according to the invention, each of which can form at least one point of contact with a contact pin. In a corresponding manner, the spring contact ring can also comprise a higher number of similar spring elements, for example four, five or six spring elements, in order to contact an inserted cylindrical contact pin at at least one contact point per existing spring element.

In one embodiment, a spring element of the spring contact ring is dumbbell-shaped in order to contact an inserted cylindrical contact pin at two different positions at the same time. In a corresponding manner, the spring contact ring can also comprise a larger number of similar spring elements, for example four, five or six spring elements, in order to contact an inserted cylindrical contact pin at at least two contact points per existing spring element.

A further aspect of the invention comprises a production method for the spring contact rings described herein. The manufacturing method comprises the formation of a spring contact ring, comprising an outer ring and a plurality of elastically deformable belt-shaped spring elements, each of which comprises two curved connectors that form a continuously running, gap-free connection between the outer ring and the respective spring element, the spring elements each extending continuously from the first connector to the second connector via a first bend, a central part of the spring element, and a second bend, wherein the central part comprises a front side which points in the direction of the central axis of the outer ring.

In one embodiment, the manufacturing process is a drawing process. In this case, the spring contact rings are produced from tubular preforms, each of which contains a removable core. The preforms according to the invention can be produced, for example, by means of spark erosion (EDM), milling, machining, laser machining, or 3D printing. In this case, for example, the outer ring and spring elements can be produced as initially separate preforms. These can then be joined together using a drawing method and can simultaneously be shaped to the desired end diameter, wherein optionally one or more annealing steps can be carried out. Individual annular parts can then be obtained from the tubular workpieces by means of a cutting or separating method. The core material can then be removed. Examples of production methods that can be used in connection with the present invention are disclosed in patent application EP3530314A1.

Alternatively, the final geometry of the spring elements according to the invention can also be produced directly by means of cutting processes, erosion processes, electrochemical removal or laser machining.

Where appropriate, the workpieces obtained can be subsequently annealed and/or a surface treatment can be carried out. Examples of surface treatments are magnetic vibratory finishing and coating processes.

A further aspect of the invention relates to a spring contact ring which can be produced by a method described above.

A further aspect of the invention relates to a medical stimulator or detector which comprises a spring contact ring as described herein.

A stimulator is a medical device which can achieve a physiological effect by sending an electrical signal to the body of a living being. For example, a neurostimulator can produce an electrical signal in the nerve cell (for example an action potential) by delivering an electrical signal to a nerve cell.

A stimulator may, for example, comprise a pulse generator, for example for use with a cardiac pacemaker or a device for neurostimulation. The invention can also be used in conjunction with stimulation or measuring electrodes for cardiac pacemaker electrodes, in particular for ventricular, atrial and left ventricular feed lines. The invention can also be used for neurostimulation, for example in spinal cord stimulation, gastric stimulation, peripheral nerve stimulation or deep brain stimulation. Furthermore, it can be used in conjunction with catheters, for example, electrophysiology applications, such as for example for ablation, cardiac current measurement or the like. Other uses are also possible, of course. Examples of catheters according to the invention are those which are designed for electrophysiological mapping or ablation of tissue. In one embodiment, the spring contact ring is configured and/or intended to be installed in a generator of an active implantable device. A spring contact ring of the invention can also be used in conjunction with a sensor, i.e. a medical device for picking up an electrical signal of the human body.

EXAMPLES

The invention is further illustrated below using examples, which, however, are to be understood as not limiting. It will be apparent to the person skilled in the art that other equivalent means may be similarly used in place of the features described here.

Figures

The figures show by way of example various embodiments of the spring contact rings described herein.

FIG. 1 shows a perspective view of a spring contact ring according to the invention. The spring contact ring comprises an outer ring 101, which comprises a plurality of spring elements 102. The outer ring 101 has an imaginary central axis 108. Each spring element 102 comprises a first connector 103 and a second connector 104 via which it in each case is directly connected to the outer ring 101. The connectors 103, 104 have a curved shape. The angle of this curvature can be approximately 90° or slightly less, for example between 75° and 90°.

In this example, the outer ring 101 and the spring elements 102 are made of the same material, namely PtIr10. The spring contact ring as a whole has a monolithic design, i.e., there is no discernible material boundary between the outer ring 101 and the spring elements 102. The two connectors 103, 104 have an essentially mirror-image shape with respect to each other and together form a trunk structure which carries the rest of the palm-shaped part of the spring element. A substantially straight part of the spring element, which extends to a first bend 106, adjoins the first connector. The angle of the first bend 106 is approximately 180°. From the first bend 106, the central part 105 of the spring element 102 extends to a second bend 107, which has a mirror-image shape with respect to the first bend 106. Their angle is also approximately 180°. The first connector 103 and the first bend 106 are each curved in the opposite direction to each other. The second connector 104 and the second bend 107 are each curved in the opposite direction to each other.

The central part 105 has a front side 109 which is arranged in the direction of the central axis 108. It serves to establish the largest electrical contact possible with a contact pin (not shown in FIG. 1), which can be inserted into the spring contact ring. Via the second bend 107, the spring element extends further via an essentially straight part to the second connector 104, which, as described above, merges directly into the outer ring 102. The spring element 102 thus extends completely linearly from a first position of the outer ring 101, where it is connected to the first connector 103, to a second position of the outer ring 101, where it is connected to the second connector 104. The spring element 102 therefore does not have a free, open end between the first connector 103 and the second connector 104.

Figure 2:
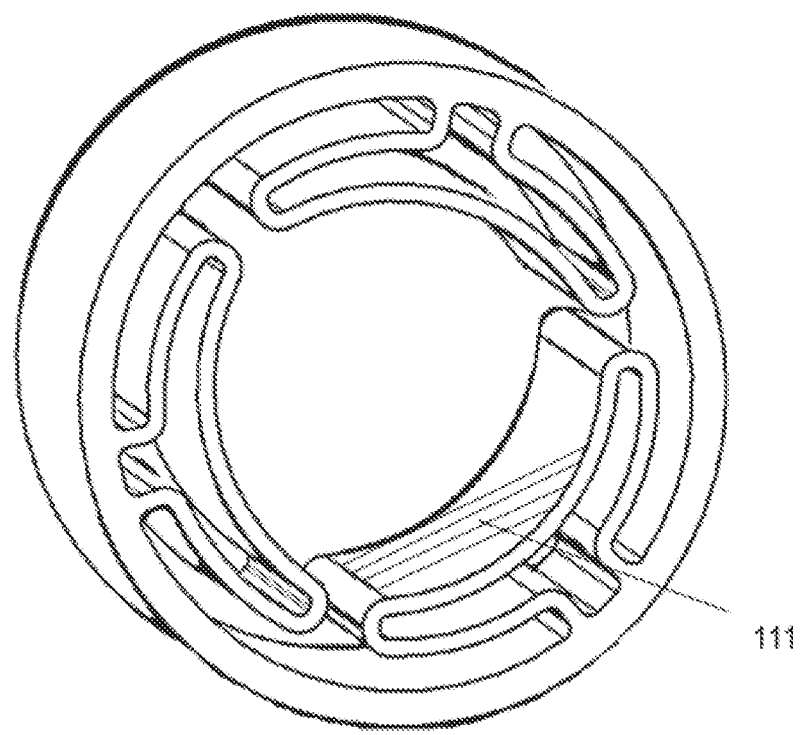
FIG. 2 shows a spring contact ring according to the invention with a thread.

FIG. 2 shows a perspective view of a further embodiment of a spring contact ring according to the invention. This embodiment is similar to that shown in FIG. 1, but additionally has a thread 111 on the front side 109 of the central part 105. With the aid of such a thread 111 a contact pin (not shown in FIG. 2) with a matching thread can be screwed into the spring contact ring.

Figure 3:
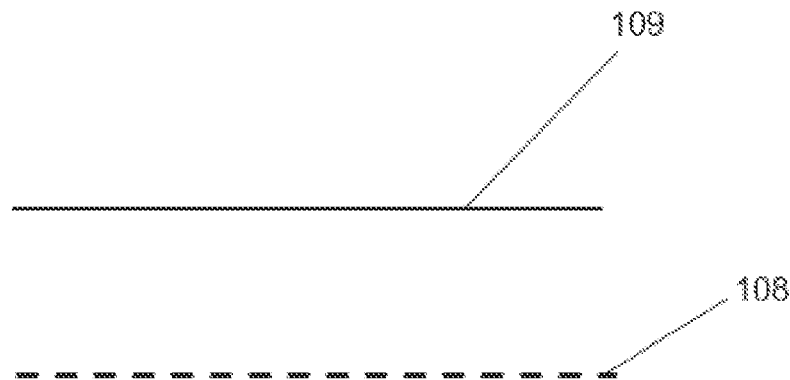
FIG. 3 shows a spring contact ring according to the invention with a spring element that extends parallel to the central axis.

FIG. 3 schematically shows an embodiment of a spring contact ring in which the front side 109 of the central part 105 is arranged parallel to the central axis 108. In this case, all points on the surface of the front side 109, which are at the same radial position, have in each case the same distance from the central axis 108.

Figure 4:
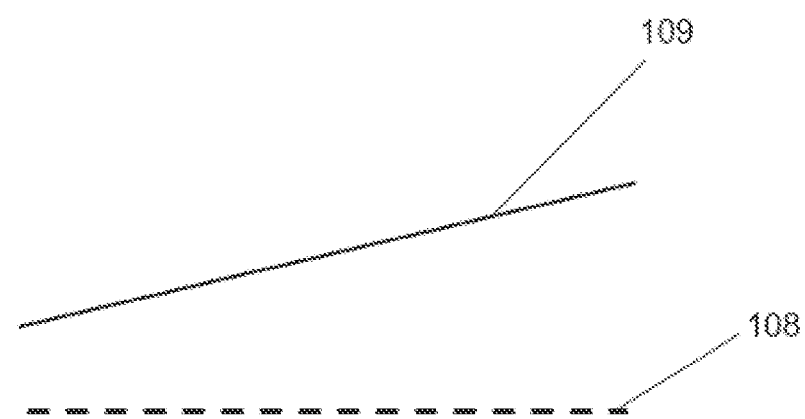
FIG. 4 shows a spring contact ring according to the invention with a spring element which extends obliquely relative to the central axis.

FIG. 4 schematically shows an embodiment of a spring contact ring in which the front side 109 of the central part 105 is arranged obliquely relative to the central axis 108. In this case, several points on the surface of the front side 109, which are located in the same radial position but at a different position in the axial direction, each have a different distance from the central axis 108.

Figure 5:
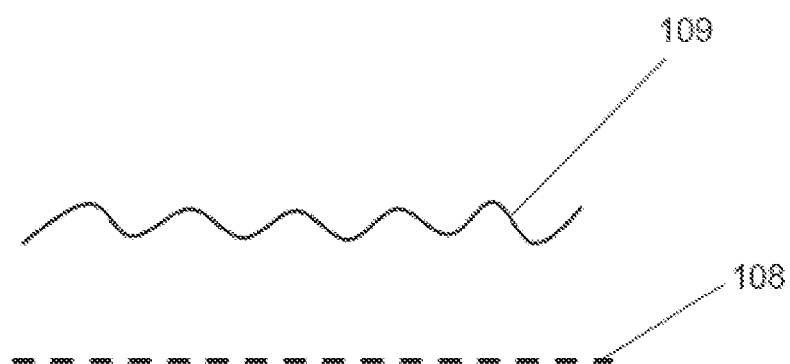
FIG. 5 shows a spring contact ring according to the invention having a spring element which has an undulating shape.

FIG. 5 schematically shows an embodiment of a spring contact ring in which the front side 109 of the central part 105 has an undulating shape. In this example, several points on the surface of the front side 109, which are located in the same axial position but at a different position in the radial direction, each have a different distance from the central axis 108.

Figure 6:
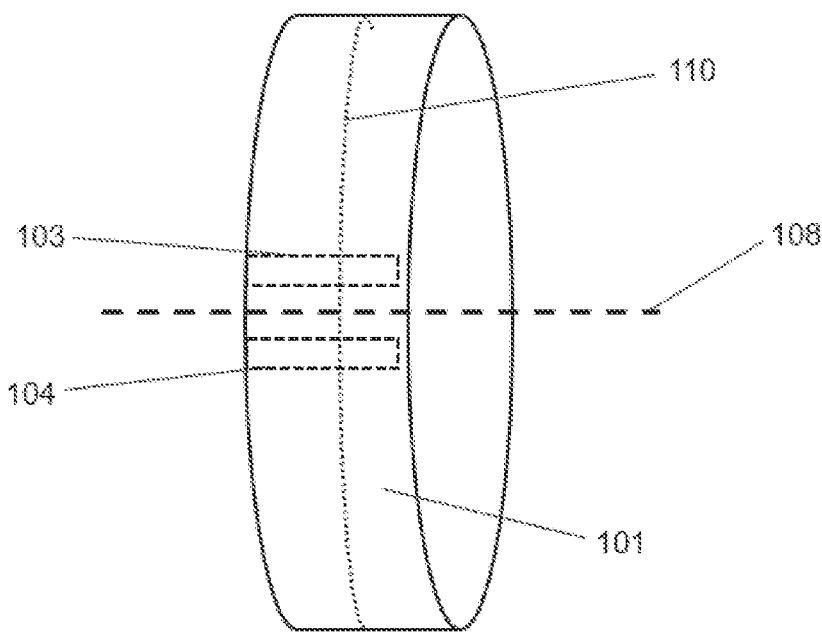
FIG. 6 illustrates the arrangement of the spring elements relative to the outer ring of the spring contact ring.

FIG. 6 schematically shows an embodiment of a spring contact ring in which the first connector 103 and the second connector 104 are arranged along a circumferential line 110 which runs on the outer ring 101 perpendicular to the central axis 108. This arrangement makes it possible to ensure that when a contact pin (not shown) is inserted, the deformation forces that occur here to act only in the radial direction on the spring element.

Figure 7:
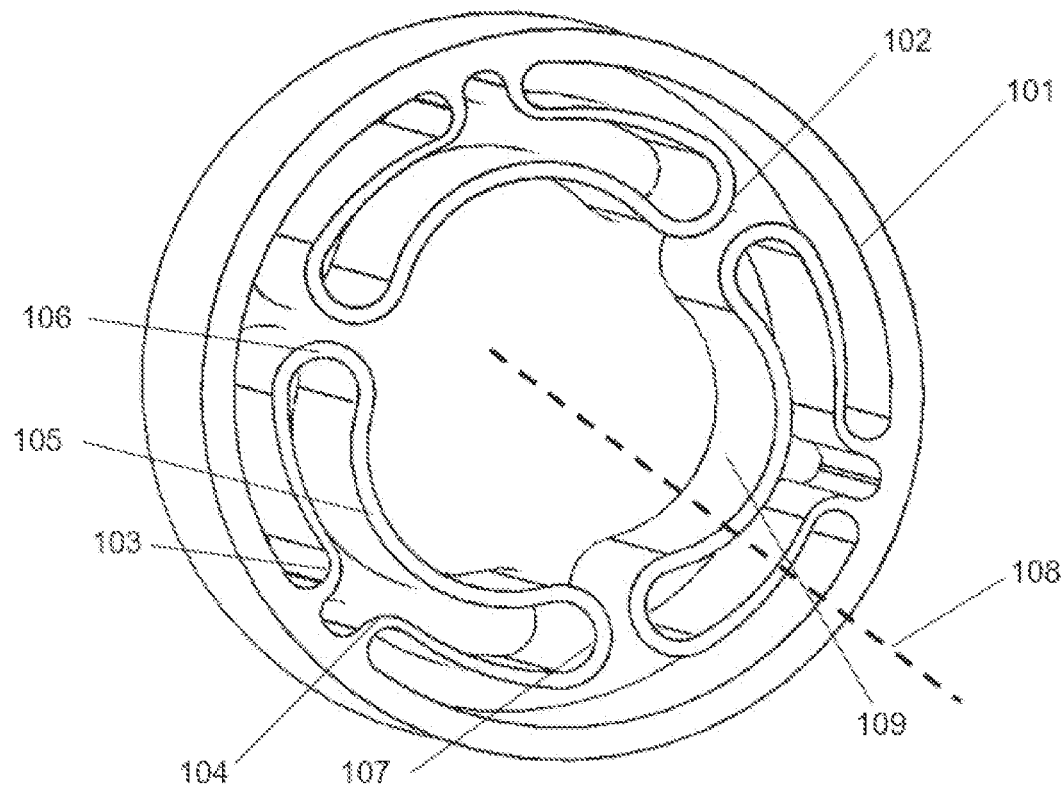
FIG. 7 shows a perspective view of a spring contact ring according to the invention having dumbbell-shaped spring elements.

FIG. 7 shows a perspective view of a spring contact ring according to the invention with dumbbell-shaped spring elements 102. In this case, the first bend 106 and the second bend 107 are designed to be more expansive than in the embodiment shown in FIG. 1 and the central part 105 is more strongly curved. This curvature is significantly more pronounced than the curvature of the outer ring 101. As a result, it can be achieved that an inserted contact pin (not shown) is contacted and held at at least two points of a spring element 102.

What is claimed is:

1. A monolithic spring contact ring for use in a medical electrode, comprising an outer ring and a plurality of elastically deformable belt-shaped spring elements, each comprising a first and second curved connector, which form a continuously running, gap-free connection between the outer ring and the respective spring element, wherein the spring elements each extend continuously from the first curved connector to the second curved connector, via a first bend, a central part of the spring element and a second bend, wherein the central part comprises a front side pointing in the direction of a central axis of the outer ring wherein the first bend is located on a first side of the first curved connector and the second bend is located a second side of the first curved connector, and wherein the first and second sides are located in opposite circumferential directions relative to the first curved connector such that the central part has a relatively long contact area.

2. A spring contact ring according to claim 1, wherein the central part is delimited and defined by the first bend and the second bend.

3. A spring contact ring according to claim 1, wherein the central part has a shape which is arranged at a uniform distance from the central axis of the outer ring.

4. A spring contact ring according to claim 1, wherein the front side has a surface parallel to the outside of the outer ring or is conical or undulating.

5. A spring contact ring according to claim 1, wherein the spring elements are arranged and configured such that essentially only radial deformation forces act on the spring elements when a cylindrical contact pin is inserted into the spring contact ring.

6. A spring contact ring according to claim 1, wherein the spring elements are arranged and configured such that the spring constant of the spring elements is largely determined by the degree of curvature of the first and second curved connectors or of the two bends.

7. A spring contact ring according to claim 1, wherein the spring elements are arranged and configured such that the spring constant of the spring elements is largely determined by their wall thickness.

8. A spring contact ring according to claim 1, wherein the front side comprises a thread.

9. A spring contact ring according to claim 1, wherein the front side comprises a section with increased wall thickness.

10. A spring contact ring according to claim 1, wherein the outer ring comprises Pt or a Pt alloy, preferably PtIr.

11. A spring contact ring according to claim 1, wherein the spring elements comprise MP35N.

12. A spring contact ring according to claim 1, which comprises exactly 2, 3, or 4 similar spring elements.

13. A spring contact ring according to claim 1, which comprises no spring element other than said spring elements.

14. A spring contact ring according to claim 1, wherein the bends have an increasing or decreasing wall thickness in the direction of the outer ring.

15. A medical pulse generator or detector, comprising a spring contact ring according to claim 1.

* * * * *